(12) United States Patent
Walsh et al.

(10) Patent No.: US 11,906,494 B1
(45) Date of Patent: *Feb. 20, 2024

(54) AUTOMATED COUPON LIFTING DEVICE

(71) Applicant: Center for Pharmaceutical Cleaning Innovation Corp., Hillsborough, NJ (US)

(72) Inventors: Andrew Walsh, Somerville, NJ (US); Isaac Downey, Manchester, MD (US)

(73) Assignee: CENTER FOR PHARMACEUTICAL CLEANING INNOVATION CORP, Hillsborough, NJ (US)

( * ) Notice: Subject to any disclaimer, the term of this patent is extended or adjusted under 35 U.S.C. 154(b) by 278 days.

This patent is subject to a terminal disclaimer.

(21) Appl. No.: 17/160,934

(22) Filed: Jan. 28, 2021

Related U.S. Application Data (63) Continuation of application No. 15/600,759, filed on May 21, 2017, now Pat. No. 10,955,396.

(60) Provisional application No. 62/339,271, filed on May 20, 2016.

(51) Int. Cl.
| | |
|---|---|
| *G01N 33/00* | (2006.01) |
| *B25J 15/00* | (2006.01) |
| *B08B 3/08* | (2006.01) |

(52) U.S. Cl.
CPC .............. *G01N 33/00* (2013.01); *B08B 3/08* (2013.01); *B25J 15/0028* (2013.01)

(58) Field of Classification Search
CPC ......... G01N 33/00; B08B 3/08; B25J 15/0028
USPC ........................................................ 73/60.11
See application file for complete search history.

(56) References Cited

U.S. PATENT DOCUMENTS

| | | | | |
|---|---|---|---|---|
| 5,846,490 | A  * | 12/1998 | Yokota ............. | G01N 35/00029 422/65 |
| 6,357,907 | B1 * | 3/2002 | Cleveland ............. | B01F 33/452 366/273 |
| 7,722,815 | B2 * | 5/2010 | Katou ..................... | B01F 31/87 422/50 |
| 2008/0072664 | A1 * | 3/2008 | Hansen .................... | G01N 1/38 422/63 |
| 2008/0318341 | A1 * | 12/2008 | Esfandiari ............. | G01N 33/558 422/400 |
| 2009/0095419 | A1 * | 4/2009 | Ammann .................. | B01L 7/52 156/702 |
| 2010/0107785 | A1 * | 5/2010 | Kugimiya ............. | G01N 27/327 73/865.7 |
| 2013/0338045 | A1 * | 12/2013 | Kalra ...................... | B01L 3/508 506/33 |

OTHER PUBLICATIONS

Non-Final Office Action issued for corresponding U.S. Appl. No. 15/600,759 dated Jan. 9, 2020.
Final Office Action issued for corresponding U.S. Appl. No. 15/600,759 dated May 26, 2020.

* cited by examiner

*Primary Examiner* — Marrit Eyassu
(74) *Attorney, Agent, or Firm* — Myers Wolin, LLC (57) ABSTRACT

A device for moving a coupon comprising a coupon retainer for retaining a coupon on which a target solution is to be tested, a coupon manipulator for engaging the coupon retained in the coupon retainer with the target solution, and a first controller for controlling a movement of the coupon manipulator.

12 Claims, 11 Drawing Sheets

STATION HARDWARE ASSY
RIGHT SIDE VIEW

FIG. 9A

STATION HARDWARE ASSY
ISOMETRIC VIEW

AUTOMATED COUPON LIFTING DEVICE

CROSS-REFERENCE TO RELATED APPLICATIONS

This application is a continuation of U.S. patent application Ser. No. 15/600,759, filed May 21, 2017, which claims priority to U.S. Provisional Application No. 62/339,271, filed May 20, 2016, the contents of each of which are incorporated by reference herein.

FIELD OF THE INVENTION

The present invention is in the technical field of surface sample analysis. More particularly, the present invention is in the technical field of Pharmaceutical cleaning process validation.

BACKGROUND

In the world of cleaning validation, accuracy, precision, and repeatability are critical to discerning a quantifiable value for the cleanability of a surface given a certain detergent. The proper identification of the correct cleaner becomes even more critical when dealing with pharmaceutical equipment and processes, which often produce medications and diagnostics that may prove fatal if contaminated with other medications. Current analyses in the cleaning validation realm are largely performed manually, leaving a much higher risk for variability within data and skewed results in addition to the inefficiency of manual processing.

An evaluation of a cleaning process for a pharmaceutical product typically consists of spiking a sample of material, known as a coupon, with a known amount of contaminant, cleaning it using conventional methods and various detergents, and probing the coupon for any remnants of the contaminant. Typically, without any automation, all coupons are immersed in corresponding cleaning solutions simultaneously, and removed simultaneously. However, traditionally, each of the immersions, timings, and extractions were performed by hand one at a time, allowing significant inconsistencies to appear between data sets.

Accordingly, current solutions in the field of cleaning and cleaning validation require time consuming tests, causing costly interruptions to productive manufacturing processes. Current solutions are often inaccurate, causing cleaning protocols to be excessive in most cases and insufficient in others.

Further, existing tests are difficult or complicated to set up and can only operate on one or a few coupons at a time.

SUMMARY

Described herein is a semi-automated electro-mechanical device programmable by a user to process multiple coupons by, among other things, depositing coupons into and removing them from a solution being tested, in order to collect statistically significant data on product cleanability. The user may select a variety of functions and input custom runtimes for any variety of products. The device may also include environmental control and monitoring features in order to best capture ideal cleaning conditions.

The subject of this patent is a device which lends itself to faster analysis and more accurate characterization of product cleanability. The device accomplishes this through at least three unique aspects. First, the device is controlled using a microcontroller which allows the device to operate independently once initial parameters are entered by the user. Second, the device incorporates a precise timing system which permits more accurate and repeatable results compared to current manual methods. Third, the device is designed in a modular manner, allowing it to be scaled to large or small applications, and allows for the insertion of additional controls within the device as necessary. Each of the three aspects described above are innovations within the field, and their combination in a single device is especially unique.

In its simplest version, the device described automates the manual process described above by providing use of a hanger system, with various hooks provided on which coupons may be placed. The hooks may be provided on a hanger rack, which may then be carefully placed above an array of beakers containing cleaning solutions, such that all attached coupons would be immersed in the beakers. A cleaning timer may then be manually monitored, and after the conclusion of a testing time, the hanger would be lifted, extracting all coupons from their solutions simultaneously. Such a device may further provide a stirring device, such as a device with multiple stirrers. Accordingly, each beaker may be placed upon a stirrer, forming the array of beakers.

DETAILED DESCRIPTION OF THE PREFERRED EMBODIMENTS

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

An automated coupon lifting device is provided for depositing coupons into, and lifting coupons out of, cleaning solutions during a cleaning validation process. Typically, such cleaning validation processes comprise comparing the effect of different detergents, detergent solutions, or cleaning processes, on a material sample, known as a coupon. Some such validation processes are designed to determine the effect of cleaning solutions on various materials, in which case the coupons may be left clean. In other validation processes, the process is designed to determine the cleanability of certain materials when they are contaminated. In such processes, these coupons are contaminated in a known way and are then cleaned using a controlled and/or automated process. The cleaning is performed in a controlled environment so that the effect of various cleaning processes can be accurately compared.

The coupon lifting device allows for the comparison of cleaning processes by controlling several parameters of cleaning. In particular, it can control agitation level, or stirring, of a cleaning solution, the time of a cleaning process, and the temperature of the cleaning solution, among other parameters.

Figures 1A, 1B:
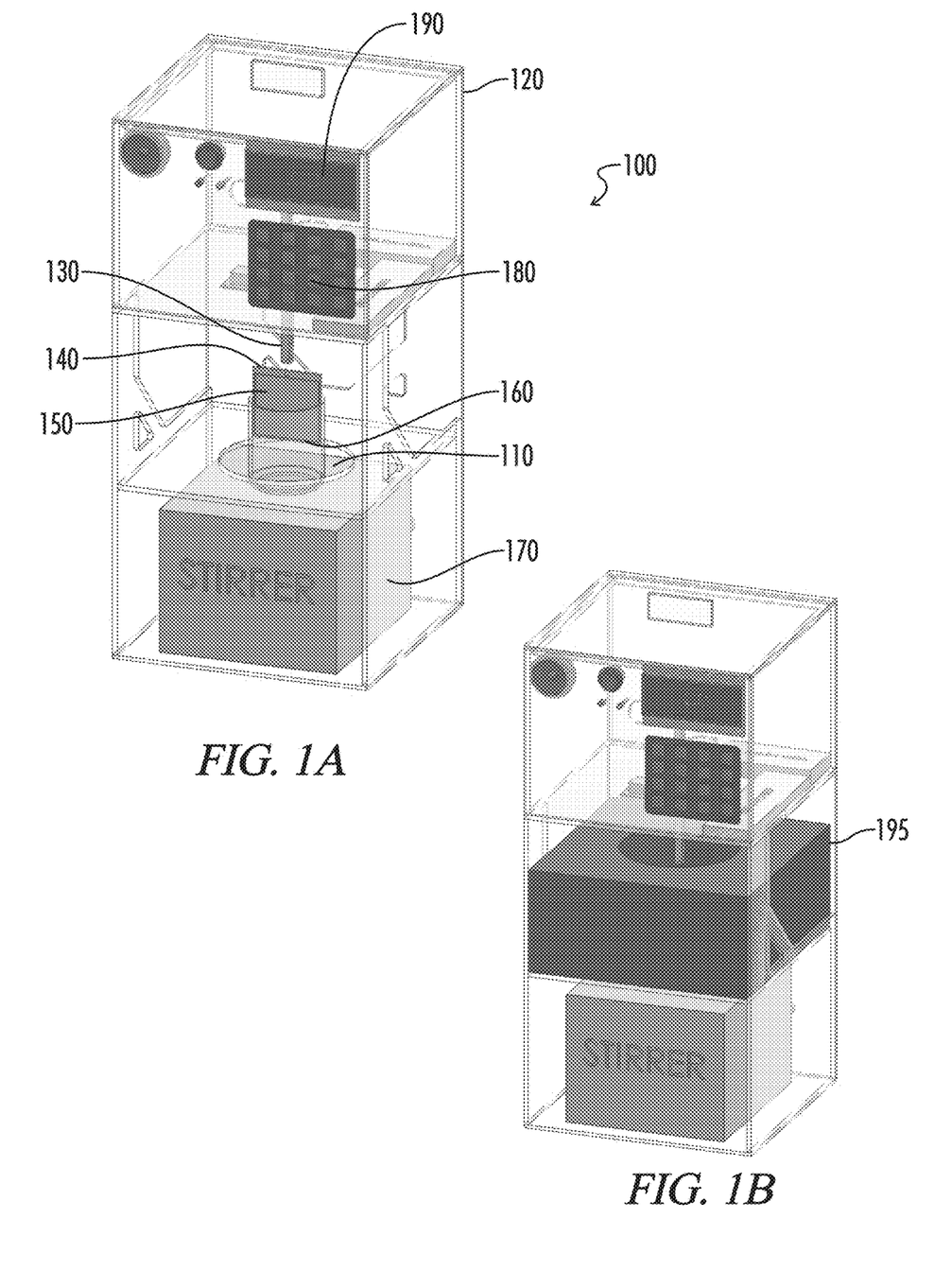
FIG. 1A is a perspective view of one embodiment of an automated coupon lifting device with a single cleaning bay.
FIG. 1B is a perspective view of a second embodiment of an automated coupon lifting device with a single cleaning bay.

FIG. 1A shows a perspective view of one embodiment of a coupon lifting device 100 having a single cleaning bay 110. A cleaning bay 110 is a location in which cleaning occurs, and may simply be a location designated for the placement of a beaker 160. It may also be an indentation for locating the beaker 160, or a hole in a shelf in a housing 120 for allowing the beaker 160 to be placed on a stirring device 170. As shown, the device 100 provides a housing 120 that contains a lifting mechanism 130, in this case a rack and pinion system attached to a motor, and the lifting mechanism ends in a coupon retainer 140. The coupon retainer 140, which may be, for example, a hook or a clip, holds a coupon 150, which is a sample of material to be cleaned, by a process being evaluated.

The cleaning bay 110 holds a beaker 160 containing a cleaning solution being tested, and a stirrer 170 for stirring the solution is located within the housing 120 and under the cleaning bay 110. The stirrer 170 is typically a magnetic stirrer, but it may be any type of stirrer for agitating a solution.

The coupon lifting device 100 further comprises a controller, typically controlled by a keypad 180, and feedback is given to a user using a display 190 and other components of a user interface. When instructed to do so, the controller lowers the lifting mechanism 130 so that the coupon 150 is immersed in the cleaning solution for a precise amount of time and then lifts the coupon out of the cleaning solution. At the same time, the controller may control the stirrer 170, such that the cleaning solution is agitated at a specified speed during the time that the coupon 150 is immersed.

While the device is described as a coupon lifting device 100 and utilizes a lifting mechanism 130, the device may manipulate coupons in ways other than lifting, and a device for manipulating the coupons may be utilized in place of a lifting mechanism. Accordingly, the coupon manipulator 130 moves the coupon 150 so as to engage and disengage the coupon with the cleaning solution.

FIG. 1B shows a second embodiment incorporating additional features into the device 100 of FIG. 1A further incorporating a heating and insulating element 195. As shown, the heating and insulating element fully encompasses the beaker 160 shown in FIG. 1A, such that the cleaning solution in the beaker is maintained at a user specified temperature. As discussed below, while a fully encompassing heating and insulating element 195 is shown, a wide variety of heaters may be implemented, such as magnetic stirrer/hot plates.

Figure 2:
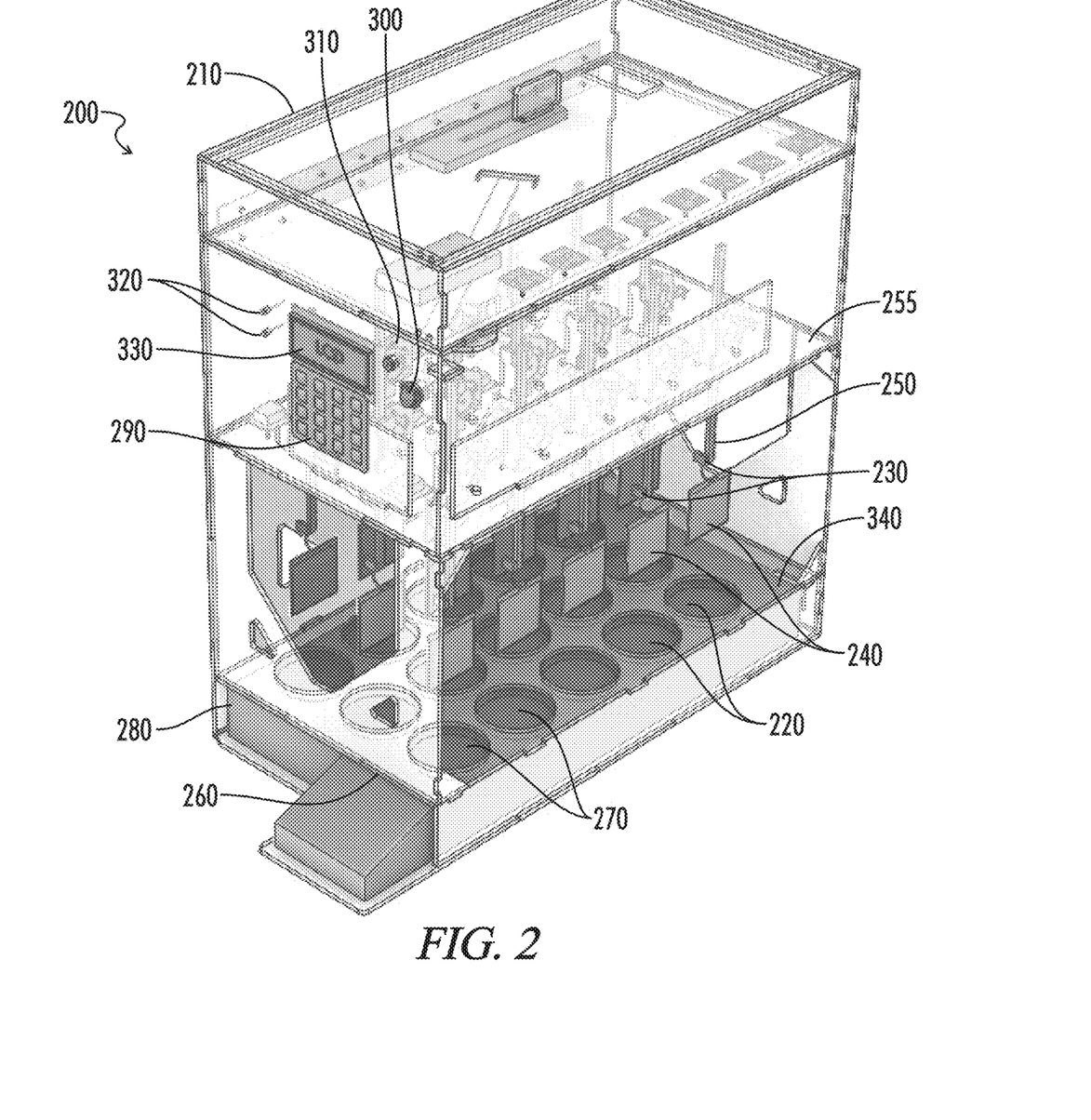
FIG. 2 is a perspective view of a third embodiment of an automated coupon lifting device having fifteen cleaning bays.
Figure 3:
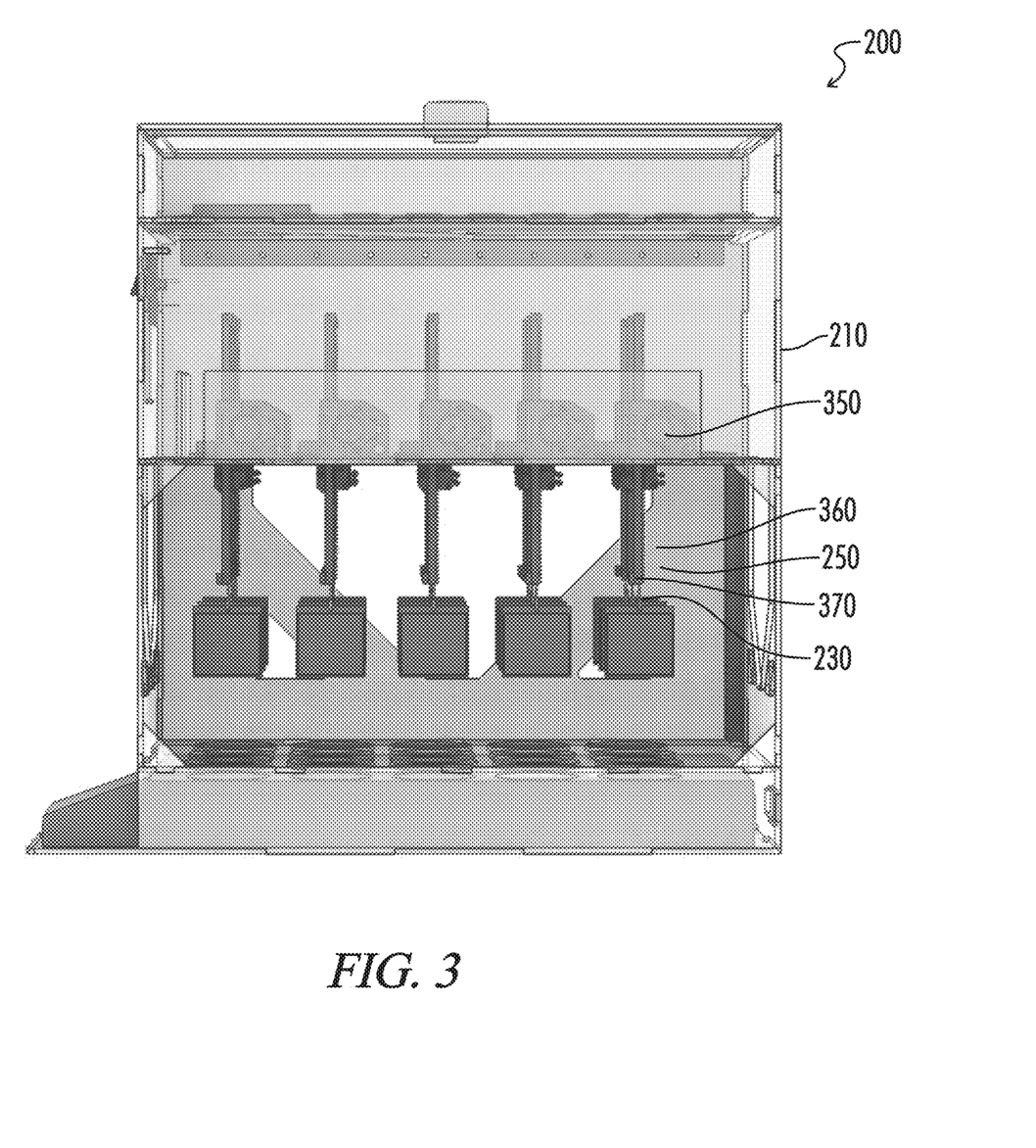
FIG. 3 is a side view of the third embodiment of the coupon lifting device of FIG. 2.
Figure 4:
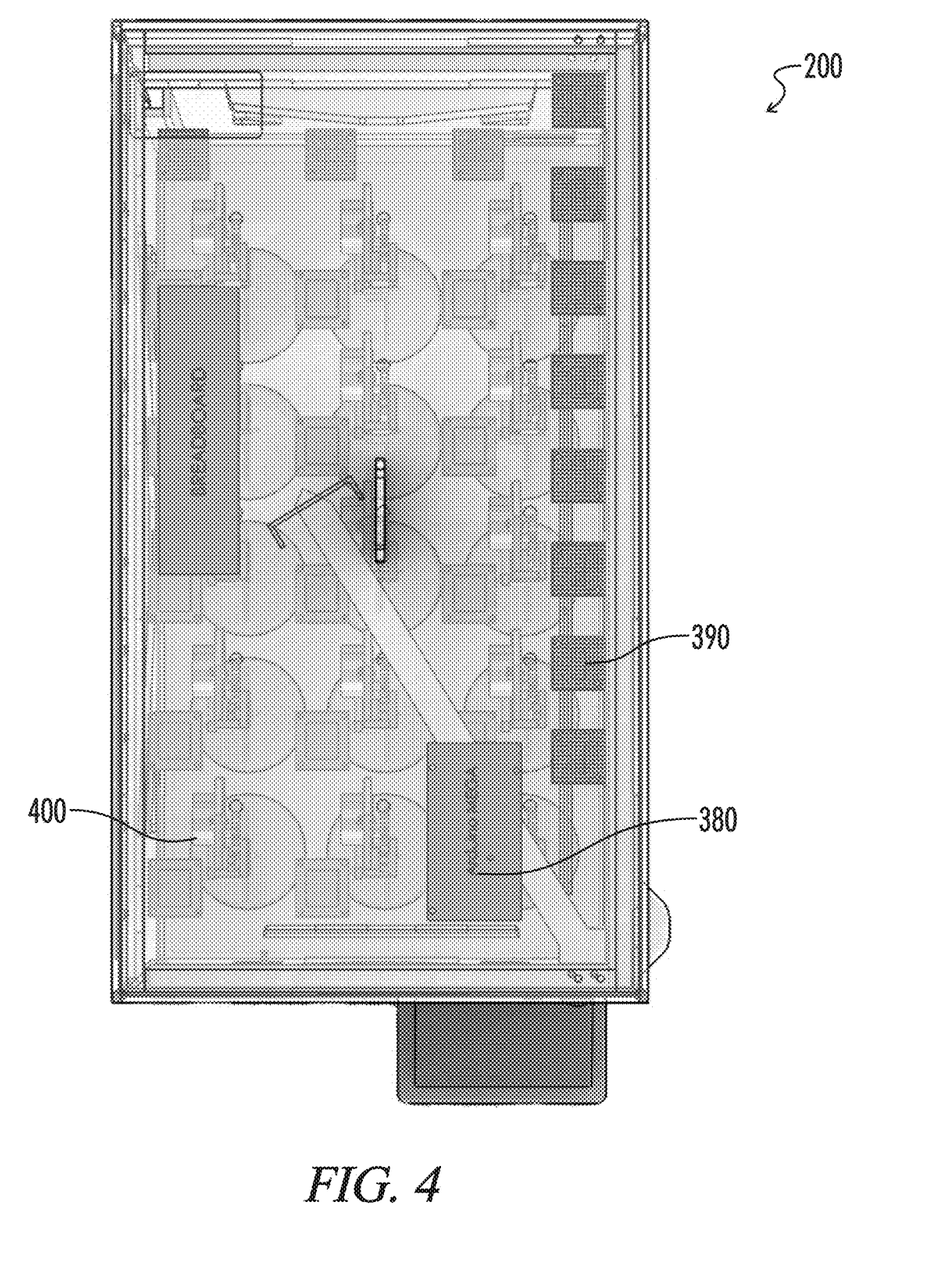
FIG. 4 is a top view of the third embodiment of the coupon lifting device of FIG. 2.

FIGS. 2-4 show a third embodiment of a coupon lifting device 200, the third embodiment containing fifteen cleaning bays 220. The device 200 provides a housing 210 that contains the cleaning bays 220, with each cleaning bay having a corresponding coupon retainer 230 for retaining coupons 240. The coupon retainers 230 are each mounted on a corresponding lifting mechanism 250, which are in turn mounted on a shelf 255 in the housing 210, and which raise and lower the coupons 240 as required by a process being implemented. While a fifteen bay embodiment is shown and described, various other numbers of bays and arrangement of bays are possible.

Each cleaning bay 220 defines a designated location for a beaker, or other container, of cleaning solution within the housing 210. The housing 210 vertically aligns each bay 220 with a corresponding lifting mechanism 250. The device 200 may further comprise a stirring device, such as a multiposition stirrer/hot plate 260 for stirring cleaning solutions located at each bay 220. The stirring plate 260 may be a fifteen position stirrer/hot plate, with one stirrer 270, such as a magnetic stirrer, corresponding to each bay 220 and lifting mechanism 250. Accordingly, each stirrer 270 stirs a cleaning solution in a beaker placed in the corresponding bay 220, and the corresponding coupon lifting mechanism 250 lowers a coupon 240 retained in its coupon retainer 230 in and out of the beaker to engage and disengage with the cleaning solution contained therein for user specified durations.

The stirrer/hot plate 260 may be integrated into the coupon lifting device 200, or the housing 210 may contain a stirring device bay 280 for retaining a third party magnetic stirrer/hot plate 260. In either case, the coupon lifting device 200 may further comprise a controller that interfaces with the stirring device 260. Accordingly, a first controller may lower each lifting mechanism 250 so that the coupon 240 is immersed in the cleaning solution at a corresponding bay 220 for a precise amount of time and then lift the coupon out of the cleaning solution. At the same time, a second controller may control the corresponding stirrer 270, such that the cleaning solution is agitated at a specified speed during the time that the coupon 240 is immersed. Typically, the first controller and the second controller are controlled from a single user interface, such that a user, at a user terminal, may coordinate the manipulation of the coupons including, in some embodiments, the actuation of the stir plate. Different control schemes may be used as well.

The controllers may be configured to vary the cleaning process applied at each bay 210 such that results of the varied processes may be easily compared. For example, the lifting mechanisms 250 at each bay 210 may be lowered simultaneously into a solution that is agitated in an identical manner by a corresponding stirrer 270, and then each coupon 240 may be lifted by the corresponding lifting mechanisms 250 consecutively at user specified intervals. In such a manner, a user can achieve fifteen samples, each of which have been subjected to a cleaning process that is identical except for a varied amounts of time spent cleaning. Similarly, the controller may vary a level of agitation applied by the stirring device 260 at each bay 210, or may perform identical processes across all fifteen bays while a user tests different solutions at each bay. Different variables may be controlled independently by the controllers, such that a wide variety of processes may be easily compared by varying settings.

In some embodiments, the device 200 is further provided with temperature sensors, such as probes mounted adjacent the coupon retainers 230, as shown below in FIG. 7 as well as heaters for controlling the temperature of the cleaning solution, as shown above in FIG. 1B. In such embodiments, the controller may use the temperature data acquired at the temperature sensors to set the temperature of the heaters. In some embodiments, such heaters may be integrated into the stirring device 260.

The device 200 may be controlled using a sixteen button keypad 290, and an on/off switch 300, while a piezoelectric buzzer 310, green and red LEDs 320, and an LCD panel 330 provide feedback to the user and comprise the device's 200 user interface. The housing 210 conceals all electrical wiring, supports the user interface, and provides a tray 340 containing the individual bays 220 to allow easy alignment of beakers of cleaning solution under the coupons 240. While a particular arrangement of controls and user interface is provided, other control solutions are possible.

The housing 210 gives a form, support, and protection to the device 200, allows the user interface to be conveniently mounted, and gives a location for the stirring device 260 to rest where the individual stirrers 270 will consistently align with the cleaning bays 220. The keypad 290 is typically used as the sole method of input from the user, while the LCD 330 is used as a visual method of conveying input information and menu options, while the LEDs 320 allow the device's status to be visually understood. An alternate input method, such as an interface with a personal computer, or an internet based interface, through a USB Port on the microprocessor, for example, is possible as well. The buzzer 310 gives the user an audio output on the status of the system, such as an indication of when a cleaning process has been completed. The stirring device 260 physically agitates the cleaning solutions consistently and allows for a coupon 240 to be tested for its cleanability within a specified process. The housing 210 may be made of extruded acrylic or any other sufficiently rigid and strong material. Variations of the device 200 will likely be produced with alternative materials.

Referring now to the device 200 as shown in FIG. 3 the device 200 can be seen from a side view, making a gear 350, a rack 360, which comprise the lifting device 250, a limit switch 370, and a coupon retainer 230 more observable. Several of these elements are more visible in FIG. 6, below.

The gear 350 and rack 360 mesh together and translate a rotational motion to a vertical linear one, allowing the coupon 240 to be lowered and elevated by its attachment to the coupon retainer 230. The limit switch 370 is used to determine the position of the rack 360 and the coupon 240 along its vertical trajectory. The coupon retainer 230 may use a variety of methods to hold the sample 240 including but not limited to magnetics, clamping, hanging by hook, Velcro, etc. The gear 350 and rack 360 pitch, diameter, and specifics may be altered without compromising the device 200, so long as the gear 350 and rack 360 are designed to properly mesh.

Referring now to FIG. 4 the device 200 can be seen from a top view, making a microcontroller 380, a shift register 390, and a motor 400 more observable.

The microcontroller 380 connects, controls, and receives inputs when applicable from all sensors and electronic components and acts as the "brain" of the device 200. The shift register 390 is chained with seven other shift registers and these are electronically connected to the microcontroller 380 in order to allow the appropriate number of pins for the motors 400 used. The motors 400 are mounted within the housing 210 and cause the rotation of the gear 350, allowing the raising and lowering of the coupon 240 to occur.

Figure 5:
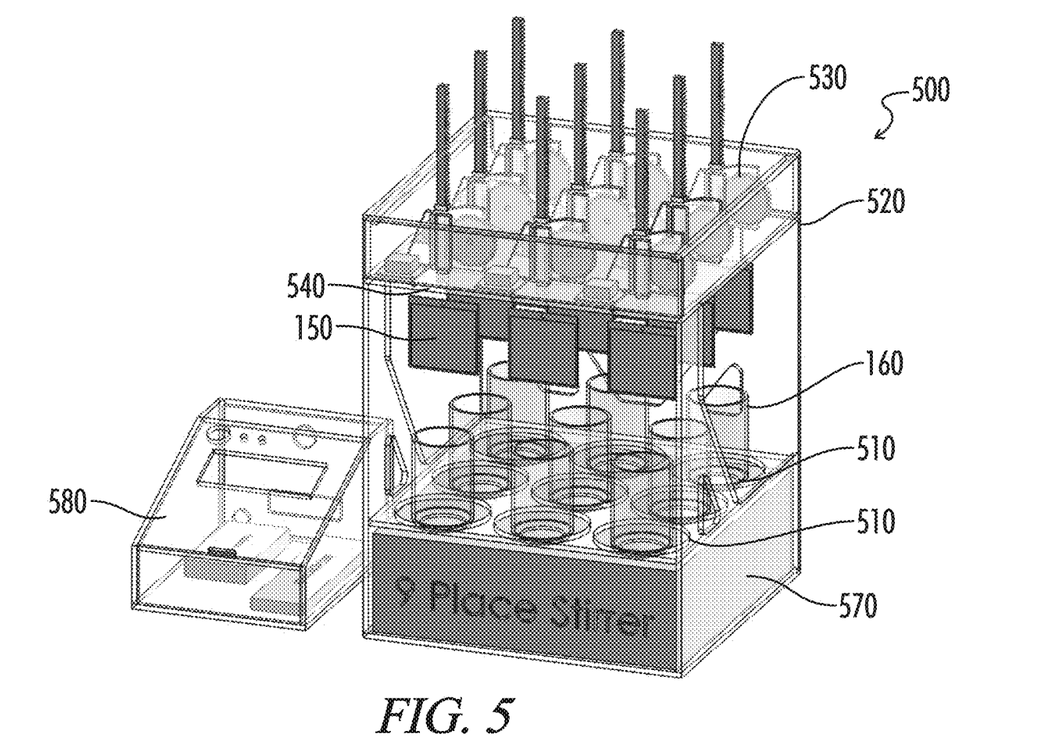
FIG. 5 is a perspective view of a fourth embodiment of a coupon lifting device having nine cleaning bays.

FIG. 5 is a perspective view of a fourth embodiment of a coupon lifting device 500 having nine cleaning bays 510, each of which are shown containing a beaker 160. As shown, the device 500 provides a housing 520 that contains nine lifting mechanisms 530, each ending in a coupon retainer 540. The coupon retainers 540 each hold a coupon 150 to be cleaned by a cleaning process being evaluated.

A nine-position stir plate 570 for stirring the solution is located within the housing 520 and under the cleaning bays 510.

The coupon lifting device 500 further comprises a control interface 580, as discussed above with respect to the device 200 of FIGS. 2-4. As shown, such an interface 580 may be placed outside of the housing 520, and may be incorporated into a larger control unit. Alternatively, it may be replaced with a computer based interface.

Figure 6:
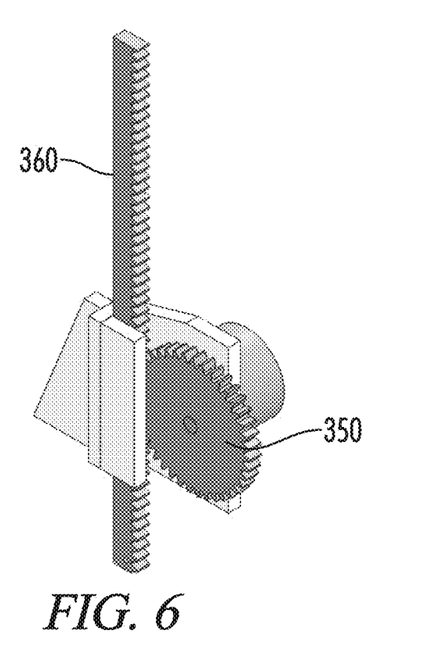
FIG. 6 is a lifting mechanism for use with an automated coupon lifting device.

FIG. 6 is a lifting mechanism 130, 250 for use with an automated coupon lifting device 100, 200, 500. As discussed with respect to FIG. 3, the mechanism 130, 250 comprises a gear 350, a rack 360. The gear 350 and rack 360 mesh together and translate a rotational motion to a vertical linear one, allowing a coupon 150, 240 contained therein to be lowered and elevated.

Figure 7:
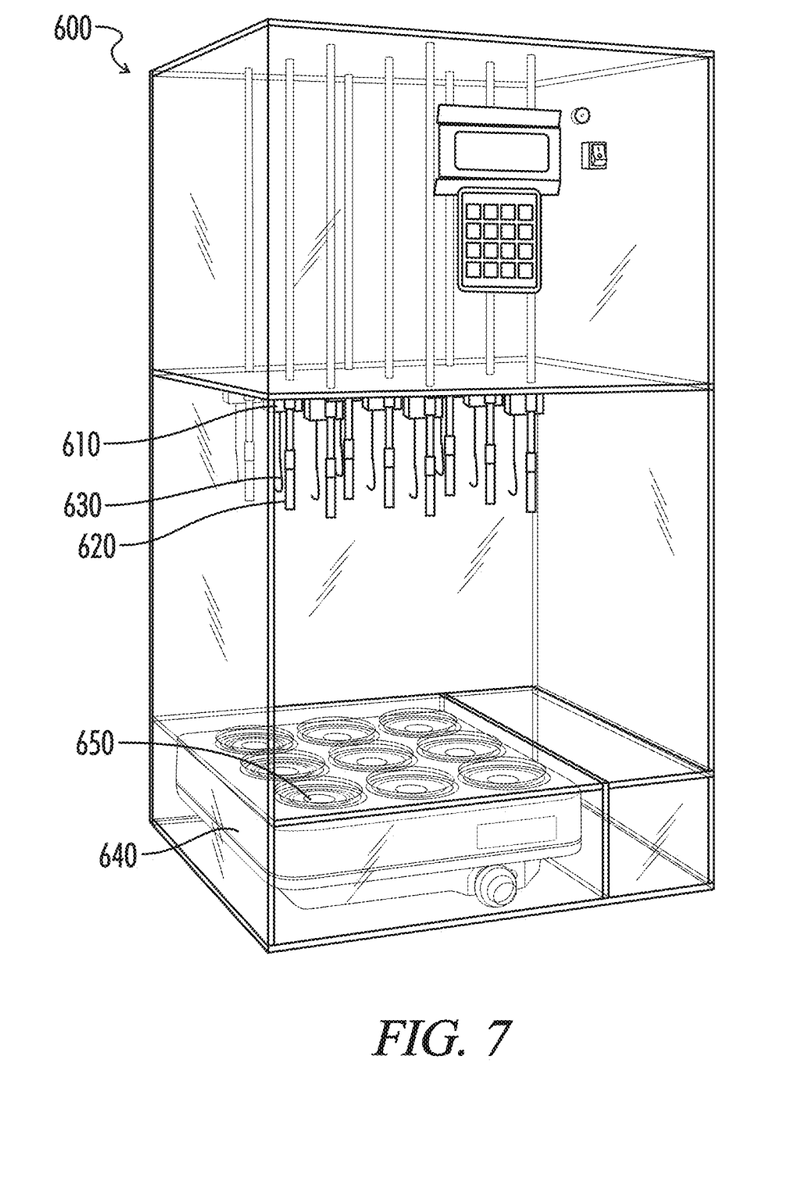
FIG. 7 is a fifth embodiment of a coupon lifting device having nine cleaning bays.

FIG. 7 is a fifth embodiment of a coupon lifting device 600, also containing nine cleaning bays. As shown, each lifting mechanism 610 may further comprise a temperature sensor 620 in addition to a coupon retainer 630. While a probe is shown, any type of temperature sensor may be used, so long as the temperature sensor can determine the temperature of a cleaning solution in a beaker in a cleaning bay. For example, a laser based temperature sensor may be mounted adjacent each lifting mechanism 610. Typically, each cleaning bay will have such a temperature sensor. Other sensors (e.g. conductivity) may be used as instead or in concert with other sensors.

The device 600 may further contain a stir tray 640 that contains heating elements in the stirrers 650, such that the controller may use the temperature data acquired at each temperature sensor 620 to set the temperature of the corresponding heating element.

Figure 8:
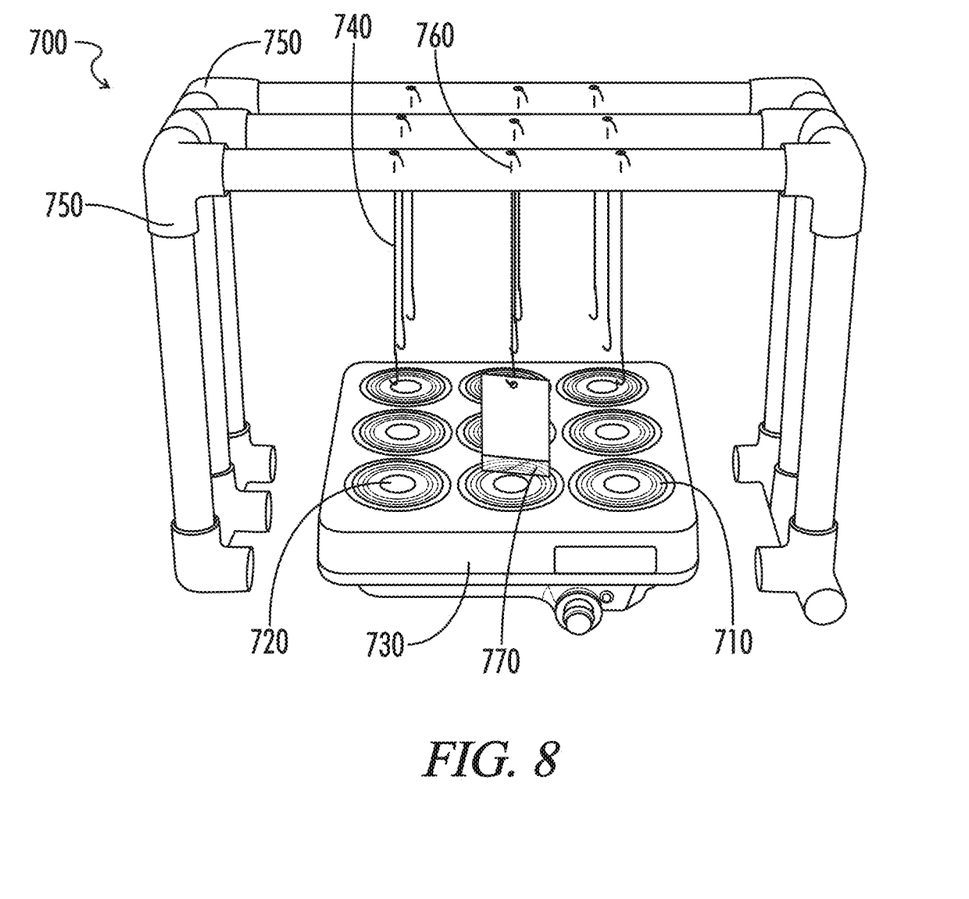
FIG. 8 is a sixth embodiment of a coupon lifting device having nine cleaning bays.

FIG. 8 is a sixth embodiment of a coupon lifting device 700 with nine cleaning bays 710. Each cleaning bay is a position in which a beaker may be placed, and in which a stirrer 720 of a stirring device 730 may be aligned with a coupon retainer 740. The device 700 comprises a frame 750 containing attachment points 760 for nine coupon retainers 740, each of which may be provided with a coupon 770 to which a cleaning process will be applied.

In order to use the coupon lifting device 700, a coupon 770 is applied to each coupon retainer 740 corresponding to a cleaning bay 710 in which a cleaning process will be evaluated. A beaker is then placed on each stirrer 720 corresponding to those cleaning bays 710. The frame 750 is then lowered onto the stirring device 730 such that each of the coupons 770 are lowered into corresponding beakers on the stirrers 720. After a specified time for the cleaning process being evaluated, the frame 750 is raised, lifting each of the coupons 770 out of corresponding beakers and making the coupons available for evaluation.

The automated coupon lifting device may use a standard microcontroller (such as, but not limited to, an Arduino Mega) as a single processor for all operations. Alternatively, different processors may be used to automate different components, while a single user interface coordinates all actions. Further descriptions here describe the embodiment shown in FIGS. 2-4, but many variations may be made in various implementations. In the embodiment shown, eight shift register (pin expansions) are used in conjunction with the microcontroller in order to satisfy the number of input/output pins for the application. A power supply with both twelve volt and five volt outputs, with maximum current ratings of two amps per line is provided. This power runs to a double pole, single throw switch which acts as the device's on/off toggle. The power supply may be used to power all components through the microcontroller, or in some cases, power may be provided directly to the motors while other components are powered through the microcontroller. A liquid crystal display (LCD) is controlled by the microcontroller to display menu options, current selections and processes, as well as user inputs. A piezoelectric buzzer is controlled to the microcontroller as an acoustic form of output to the user. Two light emitting diodes (LEDs), one red and one green, indicate the running status of the device at all times to the user. Fifteen motors and fifteen limit switches (one for each station) are wired to the shift registers which then connect to the microcontroller for control. The motors are used to facilitate the actuation of the standardized samples, while the limit switches are used to realign each position as necessary. A keypad is connected to the microcontroller to allow users to navigate the device's menu and input preferences. In order to translate the rotational motion of the motor to a linear motion, a rack and pinion gearing system is implemented at each position. Each rack includes a fastening method at its end for the standardized samples. The device may be paired with some form of agitator, in this case a fifteen position stirrer hot plate. The stirrer hot plate is inserted into the base of the device and is manually set separately from the device. The device housing is made of laser cut acrylic for faster prototyping and structural strength, but a variety of materials and forming processes are acceptable. Alternative user interfaces are contemplated, and may be implemented by controlling the device directly from a pc interface, smart phone interface or internet based interface. The particular components implemented may all be modified accordingly.

The motors used may be stepper motors geared to an appropriate ratio to allow for precise adjustments and higher torque output.

The device may be modular, such that different stirring devices may be implemented in the coupon lifting device, and that simplified versions of the device may be sold alongside more sophisticated versions with additional features. Accordingly, the microcontrollers used may be programmed to operate from only a few of their pins, to ease the addition of components and features.

Further a system for moving a coupon relative to a target solution may be provided. The system may comprise a coupon lifting device, such as those described in previous embodiments, including a housing with a bay for retaining a stir tray. The system may further comprise a stir tray for placing within the bay of the housing and a user interface or user terminal for controlling both the stir tray and the coupon lifting device.

The advantages of the embodiments described include, without limitation, more reliable and precise cleanability results for products and reducing the time and cost of the cleaning process evaluation. The embodiments also reduce the human effort and time required, allowing users of the device to increase their productivity. The Device is well suited for the use of collection of data for use in statistical analysis, allowing the collection of precise data points and simplifying the processing of sample coupons for the purpose of such analysis.

In broad embodiment, the present device is an automated cleaning device used to determine the cleanability of products relative to a certain cleaning solution. Further, while the coupon lifting device 100, 200, 500, 600, 700 is discussed in relation to a cleaning process validation device, the device may further be used to test other immersion tests, such as testing samples to determine the aversion of paints and coatings to corrosion, or the affect of a particular detergent on coupon sample materials, as well as cleaning studies in other industries.

The use of the coupon lifting device will now be described in relation to the third embodiment of the coupon lifting device 200, shown in FIGS. 2-4. In using the coupon lifting devices 200 described, a user may first provide a plurality of target solutions to be tested. The user may then position each of a plurality of coupons 240 on which the target solutions are to be tested in coupon retainers 230, where each such coupon retainer is suspended from or fixed to a lifting device 230. The lifting device 230 manipulates the coupons and moves them as required by the coupon lifting device 200.

Each coupon 240 is then located above a corresponding target solution, and is engaged with the corresponding target solution using the corresponding lifting device 230. Typically, the lifting device 230 will lower each coupon into the corresponding target solution. After a controllable amount of time, each coupon 240 is disengaged from the corresponding target solution by, for example, the lifting device 230 lifting the coupon out of the solution.

Typically, each target solution is provided in a different cleaning bay 220 and is placed on a different stirrer 270 of a stir plate 260.

In some process implementations, different target solutions are used at each of the fifteen cleaning bays 220. This may be, for example, to test the effect of different cleaning solutions used in identical processes. In such embodiments, the coupons 240 may engage the target solutions simultaneously, and may disengage the target solutions simultaneously. In other process implementations, identical target solutions may be used while each coupon 240 engages with the solution for a different amount of time. In such embodiments, the coupons 240 may engage the target solutions simultaneously and may disengage, or be removed from, the target solutions consecutively at fixed intervals. Alternatively, the coupons 240 may engage the target solutions consecutively at fixed intervals and may disengage, or be removed from, the target solutions simultaneously.

Agitation within the stirring containers may be controlled to match the level of turbulence occurring in full size cleaning processes. This may be done by precisely controlling the RPM of the stirrer motor. The RPM value is calculated using the desired Reynolds number, the standard dimensions of the stirring containers used, and the method of agitation as inputs. This best matches the cleaning that would take place while cleaning a full-sized piece of equipment.

Various interfaces may be provided. For example, a touch screen may be used as a human-machine interface (HMI) to allow the selection of input parameters for any given program, the particular program to be run, operator information, or diagnostic measures. However, the HMI is not restricted to touch screens. Alternatives to touch screens include, but are not limited to, keypads, keyboard and mouse, interface through a computer, or a series of buttons. Additional visual feedback devices include, but are not limited to liquid crystal displays (LCD's) as well as a television or computer screen.

Figure 9A:
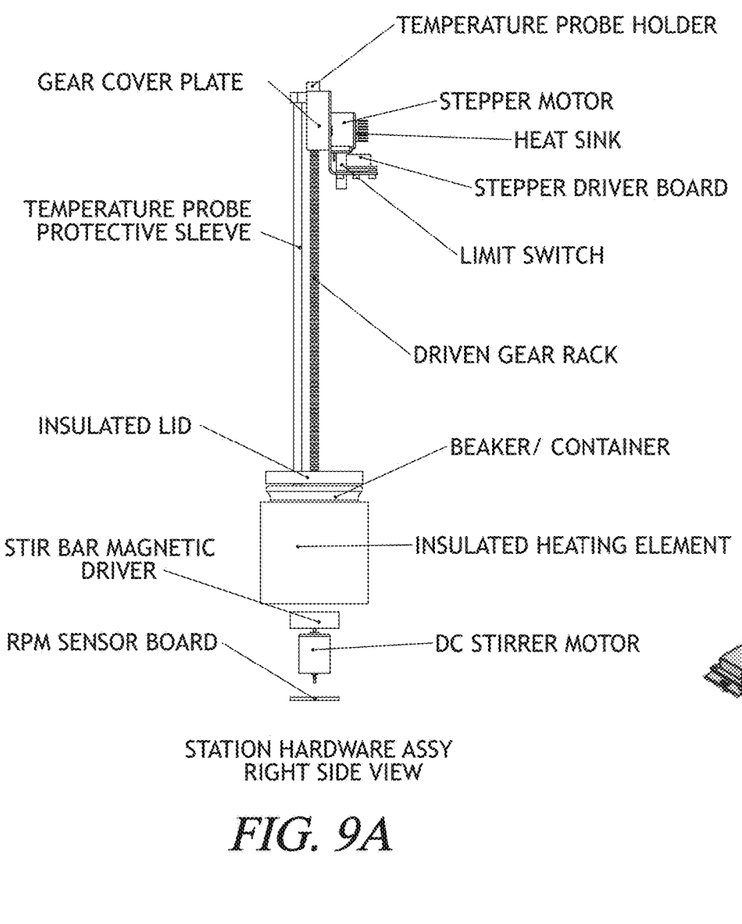
FIGS. 9A and 9B are a cleaning station for a seventh embodiment of a coupon lifting device.
Figure 9B:
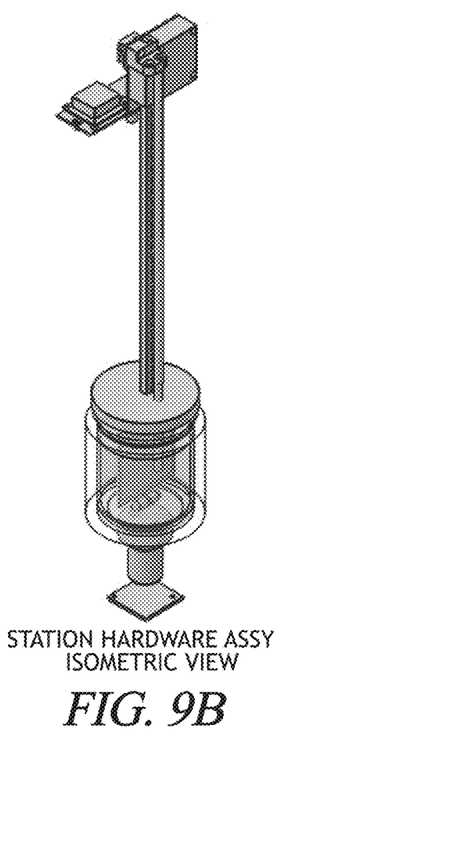

A typical cleaning station for a seventh embodiment of a coupon lifting device is shown in FIGS. 9A and 9B. Each cleaning station will typically utilize a temperature probe as well as a heating element in order to control another important variable in the cleaning process: temperature. The heating element will bring the cleaning solution to the temperature used in a cleaning process for the full-size equipment, typically up to 95° C. The temperature sensor will monitor the temperature of the cleaning solution until it has reached the user-defined value, at which point the heating elements will be turned off. The feedback system may be designed such that the heating system can maintain the cleaning solution within 0.5° C. of the desired value. This precision may be achieved by using high quality insulation to reduce heat loss from the stirring containers, as well as by using highly efficient heaters which can transfer heat to the cleaning solution directly through the stirring container via conduction. The addition of temperature control instrumentation gives the user more control over the cleaning process being tested, and adds another degree of confidence for the results of the tests performed. While temperature control is not necessary to construct an automated coupon lifting system, it may allow users to input variable temperatures at each station in order to determine the optimal temperature for cleaning equipment without wasting excess energy through heating water, thereby providing an additional valuable variable that can be tested. Temperature control also allows users to program a temperature profile over the period of immersion in order to determine the effect of unstable temperatures or surging temperatures during the cleaning process for a piece of equipment.

The automated coupon lift may be provided with the capability to collect the data throughout the duration of the test. The system may save the raw data to one file as well as generate a formal report saved to another file. These reports can include data regarding time from insertion, stirrer RPM, Reynolds number, as well as temperature within the stirring container, as well as the date and time of the program's start and the user's credentials. The report can convert the raw data into the form of useful graphs and charts for better understanding. A printer may be installed with the system to allow for automatic printing of the reports. All draw data files and report files will be saved to removable memory on the device, most likely being a flash drive, SD card, or micro SD card. The methods described above are not the only ways which the data may be collected and presented. For example, data may be streamed to a computer via a wired or internet connection, where it is logged and/or stored. The automated coupon lift takes advantage of this capability, and its method of data storage may be subject to change.

In addition to the programs previously described, the automated coupon lift may also have the ability to perform an exponential extraction. In this program, the user specifies the standard parameters (temperature, turbulence, time until first coupon is extracted), but in addition the user specifies an exponential variable which is used to scale the duration at which each coupon is extracted from its respective station. For example, if the user specifies an exponential factor of 2 for their program, the first coupon will be extracted at time x, the second at time $x^2$, the third at $x^4$, etc. This type of program is useful for situations where little is known about the cleanability of a drug or product, and will allow a more precise range to be determined for further optimization of the product's cleaning process. This program is also very useful from a statistical standpoint to determine when the quantity of product remaining is no longer considered statistically significant.

The automated coupon lift described may be designed for low power consumption. In some embodiments, the device only requires a 600W power supply to operate for heated versions of the device. In such embodiments, the large majority of this power is directed towards heating and maintaining the temperature of the stirring containers during the execution of a program. The device's efficiency may be achieved through use of high quality insulation to prevent as much heat loss as possible from the cleaning solution, as well as the use of high efficiency heating elements. In addition, the microprocessor used may be efficient in its use and regulation of power, and all lighting fixtures may use highly efficient LED technology. The speed control for the stirring motors may be done by using pulse-width modulation (PWM), which could save energy when compared to using a variable resistance or similar method to vary motor speed. The combination of these considerations could make the automated coupon lift an energy efficient and cost effective testing apparatus.

In order to ensure the safety of the user as well as others in proximity to the automated coupon lift, several safety measures may be implemented in the system. First, an over-current fuse may be installed to prevent the system from drawing excess power. This could prevent damage to the machine as well as reduce the risk of fire in the event of a short inside the machine. Second, the door to the insertion space on the machine may be monitored by a magnetic sensor. This sensor could prevent the machine from operating if the door is opened, and would thereby help prevent accidental burns or personal injury from occurring when using the device.

In order to make the system as versatile as possible, the user would be able to save and create new programs and favorite settings for existing programs on the device itself. Given the experimental and research-oriented nature of the device, users will likely be interested in modifying or creating entirely new programs for insertion and extraction of the coupons. The device will allow users to create new programs and save them for future use. For users who repeatedly use the device for a standard program, variables may be saved to allow for faster program execution and a more streamlined experience. These additional features will allow the automated coupon lift to be as useful and versatile as possible, appealing to a wide range of potential users and companies. The scope of these user defined features may change to give more control and feature additions not described here to the user.

Figure 10A:
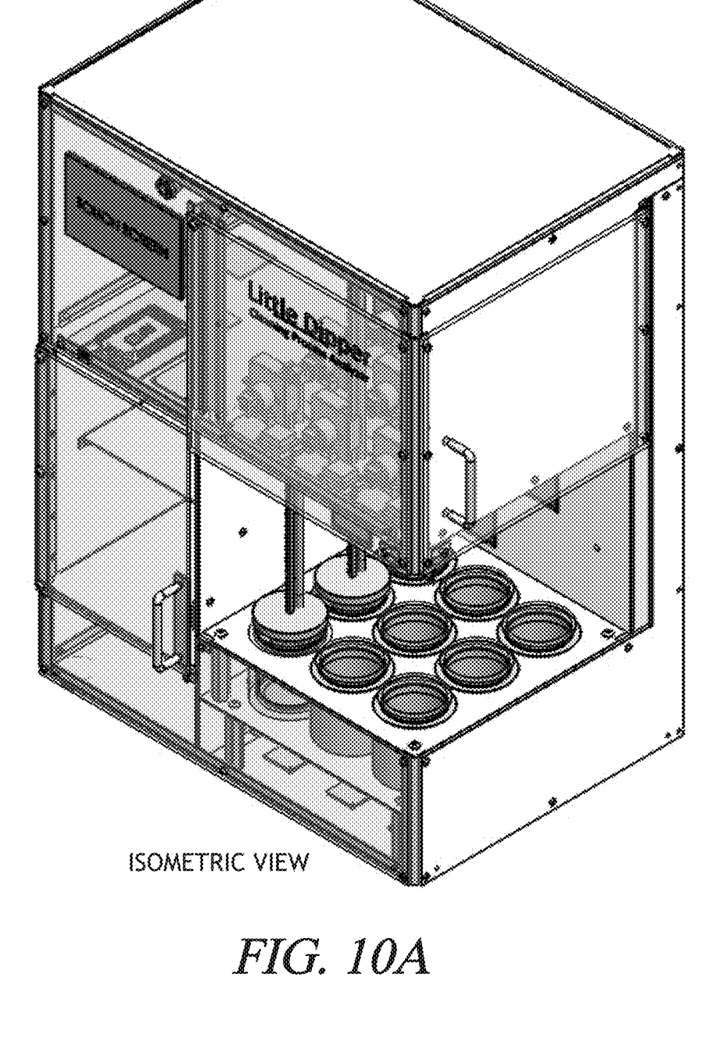
FIGS. 10A-10C are the seventh embodiment of the coupon lifting device.
Figure 10B:
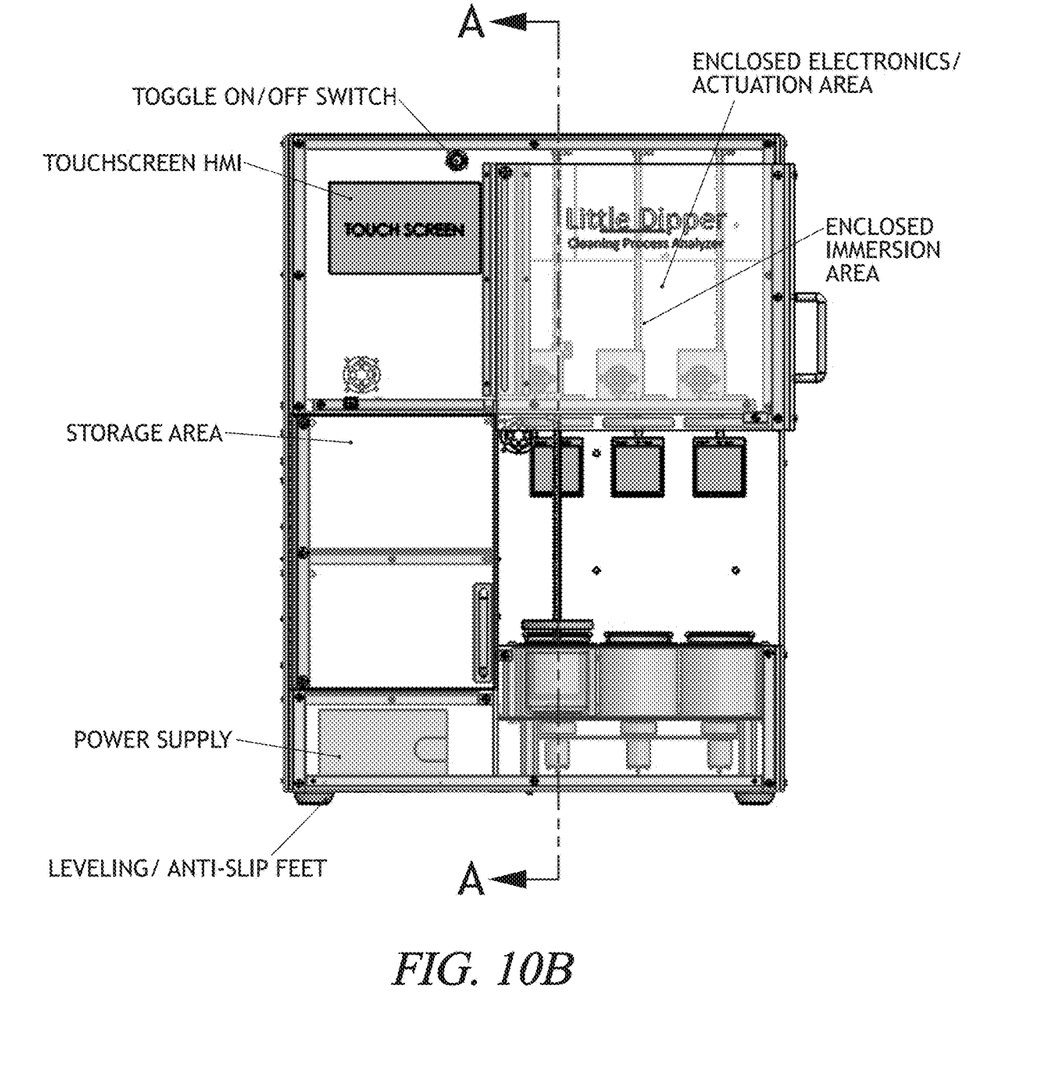
Figure 10C:
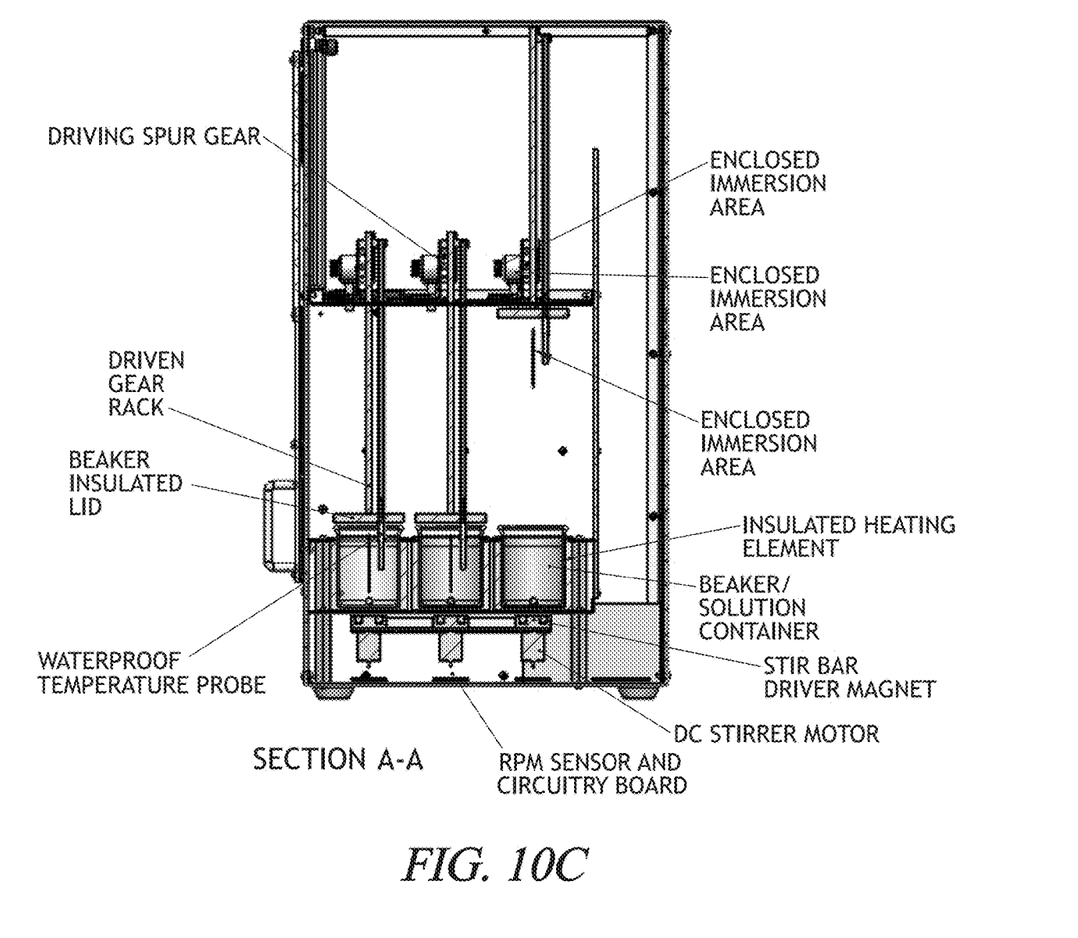

As shown in the seventh embodiment of a coupon lifting device shown in FIGS. 10A-10C, as a useful addition to the functionality of the automated coupon lifting device, the physical system may come with built-in storage space adjacent to the insertion chamber. This storage space can improve overall workflow for use of the device, as relevant materials and tools may be stored exactly where they will be used, thus reducing wasted time looking for misplaced items. The storage area can have a translucent door, allowing for maximum visibility of all items within the storage space. These features make the device more user friendly and efficient in terms of footprint. The storage space, however, is not vital to the function of the automated coupon lifting device, and the storage space could be eliminated, or a larger space could be provided in different embodiments.

Some embodiments are constructed modularly to allow for easy repair and replacement of both individual components as well as assemblies. Components may be consolidated into subassemblies wherever possible in order to make the system simpler to assemble and work on. For example, all RPM sensing circuits may be mounted to a single plate and then mounted to the base of the device. This allows much easier access to these circuits in the unlikely event of a failure. The full subassembly may be removed, the circuit in question tested and repaired or replaced, and the subassembly reinserted. This same concept may be applied for the stirring container heating elements, the stirrer motors, and the actuators, respectively. This concept also makes upgrading the device with new sensor suites much simpler, as new modules can be dropped in available spaces to further control the cleaning process. These drop-ins may include, but are not limited to, pH sensors, conductivity meters, TOC sensors, and others.

The system may, in some embodiments, connect to the internet for transferring and storing data and executing programs remotely. Such an embodiment may allow for a link between the device and a web server, offering access to certain data and report files to appropriate users, and potentially sending report emails to relevant users.

Timing for the automated coupon lift may be controlled using a precision Real Time Clock (RTC). The RTC used is accurate within several seconds over the course of a year, giving users confidence that the data collected is done to correct measures. The RTC is also used to display the date and time to users, and to time stamp reports and raw data being saved from completed programs. Timing need not be done this way, however. Using the timing on the microprocessor controller may be sufficient over short time spans, or connection to the internet or a computer would allow precise timing information to be used with the device.

The RPM of the stirrer motors may be precisely controlled using a suite of Hall-effect sensors, which use an interrupt function to indicate the number of revolutions performed over a specified duration of time. The small sample of revolutions collected over a several second period is extrapolated to determine the average RPM over that period. This is then compared to the desired RPM and returned as feedback to adjust the motor speed. There are many other viable ways the RPM could be precisely controlled. One such solution which may be implemented is a frequency to voltage (F to V) circuit. Such an approach would automatically smooth the output and reduce the processing effort for the microprocessor.

The frame of the device may be constructed from any number of suitable materials, such as by using T-nut aluminum extrusion and polycarbonate sheets. The use of this extrusion allows the layout of the device to be adjusted at any time, and allows for access to internal instrumentation. In the future, a more professional assembly will be pursued, although the number of ways the frame could be constructed are innumerable While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. A device for moving a plurality of coupons comprising:
   a plurality of coupon retainers, each for retaining a corresponding coupon on which a corresponding target solution is to be tested;
   a plurality of coupon manipulators each configured for engaging and disengaging the coupon retained in a corresponding coupon retainer with the corresponding target solution;
   a first controller for controlling a movement of at least one of the plurality of coupon manipulators,
   a plurality of temperature sensors, each for detecting a temperature associated with a corresponding target solution;
   a plurality of heaters, each heater associated with a corresponding target solution, and
   a temperature controller for independently controlling each of the plurality of heaters such that a first of the plurality of heaters maintains a first of the target solutions at a first temperature and a second of the plurality of heaters maintains a second of the target solutions at a second temperature different than the first temperature,
   wherein the first controller independently controls the movement of each of the coupon manipulators and thereby controls a time at which each coupon manipulator engages or disengages the corresponding coupon with the corresponding target solution.

2. The device of claim 1 further comprising a plurality of stirrers for stirring the target solutions, and a second controller for controlling at least one of the stirrers.

3. The device of claim 2 further comprising a housing for maintaining a position of the coupon manipulators relative to the corresponding target solutions and the stirrers, and for supporting a moving of the coupon manipulators.

4. The device of claim 2 wherein a single user interface controls the first controller and the second controller.

5. The device of claim 1, wherein the temperature controller independently controls each heater of the plurality of heaters based on temperature data acquired at the corresponding temperature sensor of the plurality of temperature sensors.

6. The device of claim 5 wherein each temperature sensor of the plurality of temperature sensors is a temperature probe adjacent at least one of the coupon retainers.

7. The device of claim 1 further comprising a plurality of independently controllable stirrers for stirring each of the plurality of target solutions and a housing for maintaining the position of each of the plurality of coupon manipulators relative to a corresponding stirrer, and wherein a second controller controls an agitation applied to each target solution by its corresponding stirrer independently and wherein the first controller disengages each coupon with the corresponding target solution simultaneously.

8. The device of claim 7 wherein each target solution contains a different detergent solution for cleaning the corresponding coupon.

9. The device of claim 1 wherein each coupon manipulator disengages its corresponding coupon from the corresponding target solution sequentially at intervals controlled by the first controller.

10. The device of claim 9 wherein the intervals are defined by an exponential variable.

11. The device of claim 1 further comprising a housing for maintaining the position of the coupon manipulators relative to the target solution, and for supporting relative movement of the coupon manipulators, wherein the housing has a plurality of stirrer bays for retaining a plurality of stirrers, and wherein the housing suspends the coupon manipulators above corresponding stirrer bays of the plurality of stirrer bays.

12. A system for moving a plurality of coupons relative to target solutions, the system comprising:
 a coupon moving device comprising:
  a plurality of coupon retainers, each for retaining a corresponding coupon on which a target solution is to be tested;
  a plurality of controllable coupon manipulators, each for engaging a corresponding coupon with a corresponding target solution by way of the corresponding coupon retainer; and
  a first controller for controlling movements of the coupon manipulators, thereby causing at least one of the coupon manipulators to engage and disengage a corresponding coupon with the corresponding target solution; and
 a stirrer comprising:
  a plurality of independently controllable stirrers, each for stirring a corresponding target solution; and
  a second controller for controlling the independently controllable stirrers, and
  a user terminal for controlling both the first and second controllers,
  wherein each of the coupon manipulators corresponds to one of the independently controllable stirrers, and
  wherein the first controller independently controls the movement of each of the coupon manipulators and thereby controls a time at which each coupon manipulator engages or disengages the corresponding coupon with the corresponding target solution.

\* \* \* \* \*